(12) United States Patent
Zuideveld et al.

(10) Patent No.: US 10,611,864 B2
(45) Date of Patent: Apr. 7, 2020

(54) SYNTHESIS OF SUBSTITUTED AMIDOBENZOATE COMPOUNDS, THE COMPOUNDS OBTAINED AND THE USE THEREOF AS PHTHALATE FREE INTERNAL ELECTRON DONOR FOR POLYMERIZATION OF OLEFINS

(71) Applicant: SABIC GLOBAL TECHNOLOGIES B.V., Bergen op Zoom (NL)

(72) Inventors: Martin Alexander Zuideveld, Kelmis (BE); Jaiprakash Brijlal Sainani, Gujarat (IN); Osamah Al-Humaidan, Riyadh (SA); Sudhakar R. Padmanabhan, Riyadh (SA); Prashant Sukumar Shinge, Bengaluru (IN); Sharankumar G. Shetty, Bangalore (IN); Abbas-Alli Ghudubhai Shaikh, Karnataka (IN)

(73) Assignee: SABIC GLOBAL TECHNOLOGIES B.V., Bergen op Zoom (NL)

(*) Notice: Subject to any disclaimer, the term of this patent is extended or adjusted under 35 U.S.C. 154(b) by 89 days.

(21) Appl. No.: 15/762,157

(22) PCT Filed: Sep. 22, 2016

(86) PCT No.: PCT/EP2016/072508
§ 371 (c)(1),
(2) Date: Mar. 22, 2018

(87) PCT Pub. No.: WO2017/050870
PCT Pub. Date: Mar. 30, 2017

(65) Prior Publication Data
US 2018/0273661 A1    Sep. 27, 2018

Related U.S. Application Data

(60) Provisional application No. 62/396,360, filed on Sep. 19, 2016.

(30) Foreign Application Priority Data

Sep. 22, 2015 (EP) .................................. 15186252

(51) Int. Cl.
*C08F 4/64* (2006.01)
*C08F 4/52* (2006.01)
(Continued)

(52) U.S. Cl.
CPC .......... *C08F 110/06* (2013.01); *C07C 231/14* (2013.01); *C07C 233/75* (2013.01);
(Continued)

(58) Field of Classification Search
CPC ....... C07C 233/88; C07C 233/75; C08F 4/52; C08F 4/64
See application file for complete search history.

(56) References Cited

U.S. PATENT DOCUMENTS 3,075,978 A * 1/1963 Speeter .............. C07D 295/088
544/159
3,549,689 A * 12/1970 Frey ..................... A61K 31/195
560/45
(Continued)

FOREIGN PATENT DOCUMENTS

EP       1273595 A1    1/2003
EP       1283222 A1    2/2003
(Continued)

OTHER PUBLICATIONS

International Search Report for International Application No. PCT/EP2016/072508, International Filing Date Sep. 22, 2016, dated Nov. 29, 2016, 3 pages.
(Continued)

*Primary Examiner* — Rip A Lee
(74) *Attorney, Agent, or Firm* — Cantor Colburn LLP

(57) ABSTRACT

The present invention relates to a compound according to Formula (I) wherein $R^1$ is a hydrocarbyl group selected from the group consisting of alkyl, alkenyl, aryl, aralkyl, and alkylaryl groups, and one or more combinations thereof; wherein $R^2$ is a hydrogen atom, an aryl group or an alkyl group; and wherein $R^3$, $R^4$, $R^5$ and $R^6$, are the same or different and are each independently a hydrogen atom, a halogen atom, a cyano group, an amino group, a hydrocarbyl group selected from the group consisting of alkyl, alkenyl, aryl, aralkyl, and alkylaryl groups or an alkoxy group, and one or more combinations thereof as internal electron donor and to a process for the synthesis of a compound according to Formula (I), wherein $R^1$ is a hydrocarbyl group selected from the group consisting of alkyl, alkenyl, aryl, aralkyl, alkoxycarbonyl and alkylaryl groups, and one or more combinations thereof; wherein $R^2$ is a hydrogen atom or an alkyl group; wherein $R^3$, $R^4$, $R^5$ and $R^6$, are the same or different and are each independently selected from a group consisting of a hydrogen atom; a hydrocarbyl, preferably, said process comprising the step of reacting a compound according to Formula (II) [$R^1$—C(=O)Cl] with a compound according to Formula (III) to obtain the compound according to Formula (I) and to the use of these compounds as internal donor in Ziegler-Natta catalysis of olefins.

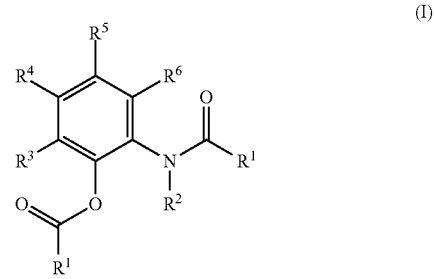

(Continued)

-continued

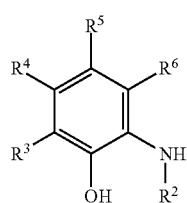
(III)

18 Claims, No Drawings

(51) Int. Cl.
  *C08F 110/06* (2006.01)
  *C07C 231/14* (2006.01)
  *C07C 233/75* (2006.01)
  *C08F 4/656* (2006.01)
  *C07C 233/88* (2006.01)

(52) U.S. Cl.
  CPC .......... *C07C 233/88* (2013.01); *C08F 4/6565* (2013.01); *C08F 2500/15* (2013.01); *C08F 2500/18* (2013.01)

(56) References Cited

U.S. PATENT DOCUMENTS

| | | | |
|---|---|---|---|
| 4,399,054 A | 8/1983 | Ferraris et al. | |
| 4,414,132 A | 11/1983 | Goodall et al. | |
| 4,472,524 A | 9/1984 | Albizzati | |
| 4,771,024 A | 9/1988 | Nestlerode et al. | |
| 4,866,022 A | 9/1989 | Arzoumanidis et al. | |
| 4,927,928 A * | 5/1990 | Shroot ................. | A61K 8/445 544/154 |
| 4,978,648 A | 12/1990 | Barbe et al. | |
| 5,077,357 A | 12/1991 | Job | |
| 5,093,415 A | 3/1992 | Brady, III et al. | |
| 5,106,806 A | 4/1992 | Job | |
| 5,550,137 A * | 8/1996 | Beeley ................. | C07C 233/29 514/354 |
| 5,556,820 A | 9/1996 | Funabashi et al. | |
| 6,825,146 B2 | 11/2004 | Kilty et al. | |
| 8,604,144 B2 * | 12/2013 | Chen ................. | C08F 10/06 526/124.3 |
| 9,440,935 B2 * | 9/2016 | Peng ................. | C07D 263/57 |
| 9,868,799 B2 * | 1/2018 | Siddiqui ............... | C08F 110/06 |
| 10,000,591 B2 * | 6/2018 | Batinas-Geurts ....... | C08L 23/12 |
| 2016/0333121 A1 * | 11/2016 | Batinas-Geurts ..... | C08F 210/16 |
| 2017/0198071 A1 * | 7/2017 | Al-Bahily ............ | C08F 110/06 |
| 2017/0240665 A1 * | 8/2017 | Zuideveld ............... | C08F 10/06 |

FOREIGN PATENT DOCUMENTS

| | | |
|---|---|---|
| WO | 9632427 A1 | 10/1996 |
| WO | 0123441 A1 | 4/2001 |
| WO | 03068828 A1 | 8/2003 |
| WO | 2006010414 A1 | 2/2006 |
| WO | 2007134851 A1 | 11/2007 |
| WO | 2010078494 A2 | 7/2010 |
| WO | 2011106494 A1 | 9/2011 |
| WO | 2014207001 A1 | 12/2014 |

OTHER PUBLICATIONS

Malamas et al., "Design and Synthesis of Aryl Diphenolic Azoles as Potent and Selective Estrogen Receptor-B Ligands", Journal of Medicinal Chemistry, vol. 47, No. 21, 2004, pp. 5021-5040.
Pullukat, Thomas J. and Hoff, Raymond E., "Silica-Bases Ziegler-Natta Catalystis: A Patent Review", Catal. Rev.-Sci. Eng. 41(3&4) pp. 389-438 (1999).
S. van der Ven; "Polypropylene and other Polyolefins"; Elsevier 1990, pp. 8-10.

* cited by examiner

SYNTHESIS OF SUBSTITUTED AMIDOBENZOATE COMPOUNDS, THE COMPOUNDS OBTAINED AND THE USE THEREOF AS PHTHALATE FREE INTERNAL ELECTRON DONOR FOR POLYMERIZATION OF OLEFINS

CROSS REFERENCE TO RELATED APPLICATIONS

This application is a National Stage application of PCT/EP2016/072508, filed Sep. 22, 2016, which claims the benefit of U.S. Provisional Application No. 62/396,360, filed Sep. 19, 2016, and European Application No. 15186252.1, filed Sep. 22, 2015, all of which are incorporated by reference in their entirety herein.

The present invention relates to novel substituted amidobenzoate compounds and the synthesis thereof. These compounds may be used as internal electron donors for use in catalyst systems for polymerization of olefins, preferably polypropylene. The invention also relates to a process for preparing said electron donors as well as the catalyst system obtained therewith; a process of making polyolefins by contacting at least one olefin with said catalyst system and to polyolefins obtainable by said process.

Catalyst systems and their components that are suitable for preparing a polyolefin are generally known. One type of such catalyst is generally referred to as Ziegler-Natta catalysts. The term "Ziegler-Natta" (Z-N) is known in the art and it typically refers to catalyst systems comprising a transition metal-containing solid catalyst compound (also typically referred to as a procatalyst); an organometallic compound (also typically referred to as a co-catalyst) and one or more electron donor compounds (e.g. external electron donors). The transition metal-containing solid catalyst compound comprises a transition metal halide (e.g. titanium halide, chromium halide, hafnium halide, zirconium halide, vanadium halide) supported on a metal or metalloid compound (e.g. a magnesium compound or a silica compound) and one or more internal electron donors. An overview of such catalyst types is for example given by T. Pullukat and R. Hoff in Catal. Rev.-Sci. Eng. 41, vol. 3 and 4, 389-438, 1999. The preparation of such a procatalyst is for example disclosed in WO96/32427 A1.

Different types of polypropylene exists, viz. (1) atactic polypropylene where the methyl groups are randomly oriented on the polymer chain, this is an amorphous polymer; (2) syndiotactic polypropylene where the methyl groups are alternatively opposite on the polymer chain, this is a semi-crystalline polymer; and (3) isotactic polypropylene where the methyl groups are all aligned on the same side of the polymer chain, this is a highly crystalline polymer. Because of its crystallinity, isotactic PP has a wide range of application in various fields, like automotive, building and construction, food packaging, medical field and so on. To achieve such a high degree of isotacticity, the prior art catalyst systems need to be improved. It is an aim of the present invention to provide novel compounds to be used as internal electron donor for improved catalyst systems. Moreover there is an on-going need in industry for phthalate free catalyst for preparing polymers and hence to phthalate free electron donors. It is an aim of the present invention to provide phthalate free electron donors. It is a further aim of the present invention to provide electron donors providing a good productivity. It is a further aim of the present invention to provide electron donors providing a low XS value. It is a further aim of the present invention to provide electron donors providing a broad MWD. One or more of the aforementioned aims of the present invention are achieved by the various aspects of the present invention.

SUMMARY OF THE INVENTION

The present invention is related to novel compounds that are suitable for use as internal electron donors in Ziegler-Natta catalysis. It has surprisingly been found by the present inventors that when used as internal electron donors in Ziegler Natta catalysis these novel, non-phthalate or phthalate free, compounds show good productivity, good XS and broad MWD.

In a first aspect, the present invention relates to a process for the synthesis of a compound according to Formula I

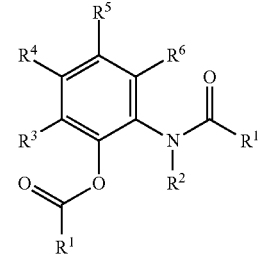

Formula I wherein $R^1$ is a hydrocarbyl group selected from the group consisting of alkyl, alkenyl, aryl, aralkyl, and alkylaryl groups, and one or more combinations thereof; wherein $R^2$ is a hydrogen atom, an aryl group or an alkyl group; and wherein $R^3$, $R^4$, $R^5$ and $R^6$, are the same or different and are each independently a hydrogen atom, a halogen atom, a cyano group, an amino group, a hydrocarbyl group selected from the group consisting of alkyl, alkenyl, aryl, aralkyl, and alkylaryl groups or an alkoxy group, and one or more combinations thereof; said process comprising the step of reacting a compound according to Formula II: $R^1$—C(=O)Cl with a compound according to Formula III

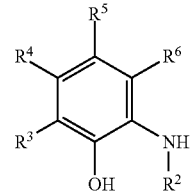

Formula III to obtain the compound according to Formula I.

In an embodiment, $R^2$ is hydrogen or methyl, preferably methyl. In an embodiment, $R^1$ is phenyl. In an embodiment, at least two, preferably at least three of $R^3$, $R^4$, $R^5$ and $R^6$, are hydrogen, more preferably $R^3$, $R^4$, and $R^6$ are hydrogen. In an embodiment, at least one of $R^3$, $R^4$, $R^5$ and $R^6$, is an alkyl, preferably a branched alkyl, more preferably tert-butyl, most preferably $R^5$ is tert-butyl. In an embodiment, $R_1$ is a halogen substituted phenyl group, for example having a chlorine, fluorine or iodine substituent at the para position and/or at the meta position and/or at the ortho position. Specific examples include p-F-phenyl and p-Cl-phenyl.

The compound according to Formula I can be considered to be a substituted 2-aminophenol compound. The compound according to Formula I is hybrid in nature due to the presence of two different heteroatoms at 1- and 2-positions of the aromatic ring system.

In an embodiment of said first aspect, a compound is provided according to Formula I wherein $R^1$=phenyl, $R^2$=methyl; $R^3$=hydrogen; $R^4$=hydrogen; $R^5$=hydrogen; and $R^6$=hydrogen, the compound being 2-(N-methylbenzamido) phenyl benzoate (denoted "ED I"). In an embodiment of said first aspect, a compound is provided according to Formula I wherein $R^1$=phenyl, $R^2$=hydrogen; $R^3$=hydrogen; $R^4$=hydrogen; $R^5$=tert-butyl; and $R^6$=hydrogen, the compound being 2-benzamide-4-(tert-butyl) phenyl benzoate (denoted "ED II"). In an embodiment of said first aspect, a compound is provided according to Formula I wherein $R^1$=phenyl, $R^2$=methyl; $R^3$=hydrogen; $R^4$=hydrogen; $R^5$=tert-butyl; and $R^6$=hydrogen, the compound being 4-(tert-butyl)-2-(N-methylbenzamido) phenyl benzoate (denoted "ED III"). In an embodiment of said first aspect, a compound is provided according to Formula I wherein $R^1$=phenyl, $R^2$=methyl; $R^3$=methyl; $R^4$=hydrogen; $R^5$=tert-butyl; and $R^6$=hydrogen, the compound being 4-(tert-butyl)-2-(N-methylbenzamido)-6-methyl phenyl benzoate (denoted "ED IV").

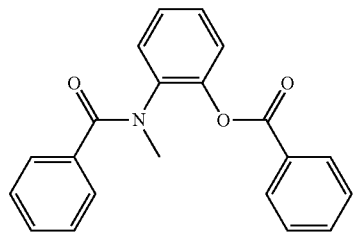

ED I

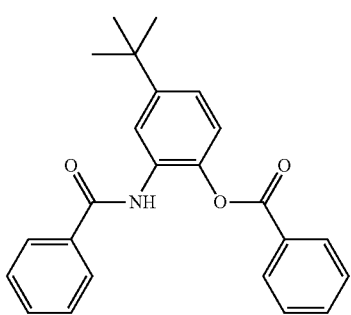

ED II

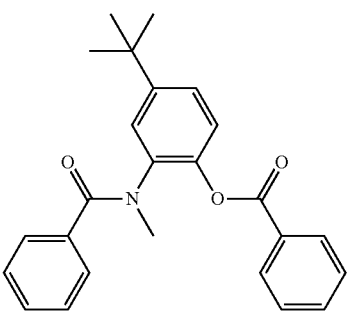

ED III

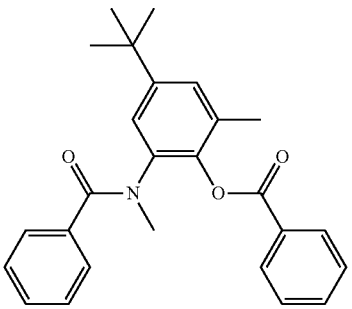

ED IV

As discussed above, the present invention relates to a process for the synthesis of these compounds. Said process is related to the synthesis of a compound according to Formula I, wherein $R^1$; $R^2$; $R^3$, $R^4$, $R^5$ and $R^6$ are as defined above; said process comprising the step of reacting a compound according to Formula II with a compound according to Formula III to obtain the compound according to Formula I.

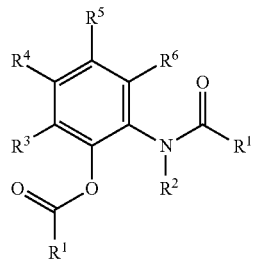

Formula I $R^1$—C(=O)Cl

Formula II

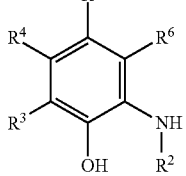

Formula III

The key to the inventive process is the reaction between a compound of Formula II ($R^1$—C(=O)Cl) and a compound of Formula III, being a substituted-2-aminophenol. In an embodiment of said second aspect, a base is used, preferably a trialkyl amine, more preferably triethyl amine. In an embodiment of said second aspect, preferably an inert solvent is used as the solvent in the process to prepare the novel compounds, more preferably selected from the group consisting of dichloromethane, xylene, cyclohexene toluene.

In an embodiment of said second aspect, in Formula III, $R^2$ is hydrogen or methyl, preferably methyl. The compound according to Formula III may be commercially obtained or prepared in a separate step preceding the process according to the present invention. Reaction conditions during this step may be determined by a person skilled in the art. As a solvent DMF and THF may for example be mentioned. In a further embodiment of said second aspect, in Formula II $R^1$ is phenyl.

In a further embodiment of said second aspect, in Formula III at least two, preferably at least three of $R^3$, $R^4$, $R^5$ and $R^6$, are hydrogen, more preferably $R^3$, $R^4$, and $R^6$ are hydrogen. In a further embodiment of said second aspect, in Formula III at least one of $R^3$, $R^4$, $R^5$ and $R^6$, is an alkyl, preferably a branched alkyl, more preferably tert-butyl, most preferably $R^5$ is tert-butyl.

In an embodiment of said process, a compound according to Formula I wherein $R^1$=phenyl, $R^2$=methyl; $R^3$=hydrogen; $R^4$=hydrogen; $R^5$=hydrogen; and $R^6$=hydrogen may be prepared, the compound being 2-(N-methylbenzamido) phenyl benzoate (denoted "ED I") as shown above. The synthesis of this specific embodiment is as follows. As a compound according to Formula II ($R^1$—C(=O)Cl) benzoyl chloride is used, wherein $R^1$ is phenyl. As a compound according to Formula III 2-(methylamino)phenol is used, wherein $R^2$=methyl; $R^3$=hydrogen; $R^4$=hydrogen; $R^5$=hydrogen; and $R^6$=hydrogen. Preferably, the solvent used is toluene. Preferably, as a base triethyl amine is used.

In an embodiment of said process, a compound according to Formula I wherein $R^1$=phenyl, $R^2$=hydrogen; $R^3$=hydrogen; $R^4$=hydrogen; $R^5$=tert-butyl; and $R^6$=hydrogen, may be prepared, the compound being 2-benzamide-4-(tert-butyl)phenyl benzoate (denoted "ED II") as shown above. The synthesis of this specific embodiment is as follows. As a compound according to Formula II ($R^1$—C(=O)Cl) benzoyl chloride is used, wherein $R^1$ is phenyl. As a compound according to Formula III 2-amino-4-(tert-butyl) phenol is used, wherein $R^2$=hydrogen; $R^3$=hydrogen; $R^4$=hydrogen; $R^5$=tert-butyl; and $R^6$=hydrogen. Preferably, the solvent used is toluene. Preferably, as a base triethyl amine is used.

In an embodiment of said process, a compound according to Formula I wherein $R^1$=phenyl, $R^2$=methyl; $R^3$=hydrogen; $R^4$=hydrogen; $R^5$=tert-butyl; and $R^6$=hydrogen, may be prepared, the compound being 4-(tert-butyl)-2-(N-methylbenzamido) phenyl benzoate (denoted "ED III") as shown above. The synthesis of this specific embodiment is as follows. As a compound according to Formula II ($R^1$—C(=O)Cl) benzoyl chloride is used, wherein $R^1$ is phenyl. As a compound according to Formula III 4-(tert butyl)-2-aminophenol is used, wherein $R^2$=methyl; $R^3$=hydrogen; $R^4$=hydrogen; $R^5$=tert-butyl; and $R^6$=hydrogen. Preferably, the solvent used is toluene. Preferably, as a base triethyl amine is used.

The 4-(tert butyl)-2-aminophenol (Formula III) may be commercially obtained or prepared in a separate step preceding the process according to the present invention, for example as discussed in the Examples below, comprising the reaction between 4-(tert-butyl)-2-aminophenol and methyl iodide, preferably using a base, such as sodium hydrogen carbonate, and preferably in a solvent, such as DMF.

In an embodiment of said process, a compound according to Formula I wherein $R^1$=phenyl, $R^2$=methyl; $R^3$=methyl; $R^4$=hydrogen; $R^5$=tert-butyl; and $R^6$=hydrogen, may be prepared, the compound being 4-(tert-butyl)-2-(N-methylbenzamido)-6-methyl phenyl benzoate (denoted "ED IV") as shown above. The synthesis of this specific embodiment is as follows. As a compound according to Formula II ($R^1$—C(=O)Cl) benzoyl chloride is used, wherein $R^1$ is phenyl. As a compound according to Formula III 4-(tert-butyl)-2-(methylamino) phenol is used, wherein $R^2$=methyl; $R^3$=methyl; $R^4$=hydrogen; $R^5$=tert-butyl; and $R^6$=hydrogen. Preferably, the solvent used is toluene. Preferably, as a base triethyl amine is used.

The 4-(tert butyl)-2-(methylamino) phenol (Formula III) may be commercially obtained or prepared in a separate step preceding the process according to the present invention, for example as discussed in the Examples below, comprising the reaction between 4-(tert-butyl)-6-methyl-2-aminophenol and methyl iodide, preferably using a base, such as sodium hydrogen carbonate, and preferably in a solvent, such as DMF.

Preferably, the temperature during the process to prepare the novel compounds is between 0 and 140° C. Preferably, the pressure during the process to prepare the novel compounds is atmospheric pressure. Preferably, the reaction time of the process to prepare the novel compounds is between 2 and 15 hours.

In an aspect, the invention relates to the use of a compound according to Formula I wherein $R^1$ is a hydrocarbyl group selected from the group consisting of alkyl, alkenyl, aryl, aralkyl, and alkylaryl groups, and one or more combinations thereof; wherein $R^2$ is a hydrogen atom, an aryl group or an alkyl group; and wherein $R^3$, $R^4$, $R^5$ and $R^6$, are the same or different and are each independently a hydrogen atom, a halogen atom, a cyano group, an amino group a hydrocarbyl group selected from the group consisting of alkyl, alkenyl, aryl, aralkyl, and alkylaryl groups or an alkoxy group, and one or more combinations thereof as an internal electron donor in a Ziegler-Natta type catalyst system. In an embodiment the invention relates to the use of a compound according to Formula I wherein $R^1$=phenyl, $R^2$=methyl; $R^3$=hydrogen; $R^4$=hydrogen; $R^5$=hydrogen; and $R^6$=hydrogen, the compound being 2-(N-methylbenzamido) phenyl benzoate; or wherein $R^1$=phenyl, $R^2$=hydrogen; $R^3$=hydrogen; $R^4$=hydrogen; $R^5$=tert-butyl; and $R^6$=hydrogen, the compound being 2-benzamide-4-(tert-butyl) phenyl benzoate; or wherein $R^1$=phenyl, $R^2$=methyl; $R^3$=hydrogen; $R^4$=hydrogen; $R^5$=tert-butyl; and $R^6$=hydrogen, the compound being 4-(tert-butyl)-2-(N-methylbenzamido) phenyl benzoate; or wherein $R^1$=phenyl, $R^2$=methyl; $R^3$=methyl; $R^4$=hydrogen; $R^5$=tert-butyl; and $R^6$=hydrogen, the compound being 4-(tert-butyl)-2-(N-methylbenzamido)-6-methyl phenyl benzoate; as an internal electron donor in a Ziegler-Natta type catalyst system.

In an aspect, the invention relates to a Ziegler-Natta type procatalyst comprising Ti, Mg, a halogen, an internal electron donor being a compound according to Formula I. In an aspect, the invention relates to a catalyst system for the polymerization of olefins, comprising a Ziegler-Natta type procatalyst according to the invention; a co-catalyst; and an external donor. In an aspect, the invention relates to a process for preparing a polyolefin by contacting an olefin with the catalyst system according to the invention, the olefin being preferably propylene. In an aspect, the invention relates to a polyolefin obtained by or obtainable by the process according to the invention. These aspects and embodiments will be described in more detail below.

Definitions

The following definitions are used in the present description and claims to define the stated subject matter. Other terms not cited below are meant to have the generally accepted meaning in the field.

"Ziegler-Natta catalyst" as used in the present description means: a transition metal-containing solid catalyst compound comprises a transition metal halide selected from titanium halide, chromium halide, hafnium halide, zirconium halide, and vanadium halide, supported on a metal or metalloid compound (e.g. a magnesium compound or a silica compound).

"internal donor" or "internal electron donor" or "ID" as used in the present description means: an electron-donating compound containing one or more atoms of oxygen (O) and/or nitrogen (N).

"external donor" or "external electron donor" or "ED" as used in the present description means: an electron-donating compound used as a reactant in the polymerisation of olefins.

"activator" as used in the present description means: an electron-donating compound containing one or more atoms of oxygen (O) and/or nitrogen (N) which is used during the synthesis of the procatalyst prior to the addition of an internal donor.

"activating compound" as used in the present description means: a compound used to activate the solid support prior to contacting it with the catalytic species.

"modifier" or "Group 13- or transition metal modifier" as used in the present description means: a metal modifier comprising a metal selected from the metals of Group 13 of the IUPAC Periodic Table of elements and transition metals.

"procatalyst" as used in the present description means: a component of a catalyst composition generally comprising a solid support, a transition metal-containing catalytic species and one or more internal donors.

"halide" or "halogen" as used in the present description means: an ion selected from the group of: fluoride (F—), chloride (Cl—), bromide (Br—) or iodide (I—).

"heteroatom" as used in the present description means: an atom other than carbon or hydrogen, preferably F, Cl, Br, I, N, O, P, B, S or Si.

"hydrocarbyl" as used in the present description means: a substituent containing hydrogen and carbon atoms, it may be a linear, branched or cyclic, saturated or unsaturated aliphatic radical, such as alkyl, alkenyl, alkadienyl and alkynyl; alicyclic radical, such as cycloalkyl, cycloalkadienyl cycloalkenyl; aromatic radical, such as monocyclic or polycyclic aromatic radical, as well as combinations thereof, such as alkaryl and aralkyl. A "substituted hydrocarbyl" is a hydrocarbyl group that is substituted with one or more non-hydrocarbyl substituent groups, such as a heteroatom.

"alkyl" as used in the present description means: an alkyl group being a functional group or side-chain consisting of carbon and hydrogen atoms having only single bonds. An alkyl group may be straight or branched and may be un-substituted or substituted.

"aryl" as used in the present description means: an aryl group being a functional group or side-chain derived from an aromatic ring. An aryl group and may be un-substituted or substituted with straight or branched hydrocarbyl groups. An aryl group may also be substituted by one or more halogen atoms. An aryl group also encloses alkaryl groups wherein one or more hydrogen atoms on the aromatic ring have been replaced by alkyl groups. An "aralkyl" as used in the present description means: an arylalkyl group being an alkyl group wherein one or more hydrogen atoms have been replaced by aryl groups.

"alkoxide" or "alkoxy" as used in the present description means: a functional group or side-chain obtained from a alkyl alcohol. It consists of an alkyl bonded to a negatively charged oxygen atom.

"aryloxide" or "aryloxy" or "phenoxide" as used in the present description means: a functional group or side-chain obtained from an aryl alcohol. It consists of an aryl bonded to a negatively charged oxygen atom.

"Grignard reagent" or "Grignard compound" as used in the present description means: a compound or a mixture of compounds of formula $R_zMgX_{2-z}$ (R is a hydrocarbyl group, $0<z<2$, X is a halide) or it may be a complex having more Mg clusters, e.g. $R_4Mg_3Cl_2$.

"polymer" as used in the present description means: a chemical compound comprising repeating structural units, wherein the structural units are monomers.

"monomer" as used in the present description means: a chemical compound that can undergo polymerization.

"olefin" as used in the present description means: an alkene. "olefin-based polymer" or "polyolefin" as used in the present description means: a polymer of one or more alkenes.

"propylene-based polymer" as used in the present description means: a polymer of propylene and optionally a comonomer. "polypropylene" as used in the present description means: a polymer of propylene.

"copolymer" as used in the present description means: a polymer prepared from two or more different monomers.

"MWD" or "Molecular weight distribution" as used in the present description means: the same as PDI or polydispersity index. It is the ratio of the weight-average molecular weight (Mw) to the number average molecular weight (Mn), viz. Mw/Mn, and is used as a measure of the broadness of molecular weight distribution of a polymer. Mw and Mn are determined by GPC using a Waters 150° C. gel permeation chromatograph combined with a Viscotek 100 differential viscosimeter; the chromatograms were run at 140° C. using 1,2,4-trichlorobenzene as a solvent; the refractive index detector was used to collect the signal for molecular weights.

"XS" or "xylene soluble fraction" as used in the present description means: the weight percentage (wt. %) of soluble xylene in the isolated polymer, measured according to ASTM D 5492-10.

"bulk density" as used in the present description means: the weight per unit volume of a material. Bulk density is measured as apparent density according to ASTM D1895-96 Reapproved 2010-e1, test method A.

"polymerization conditions" as used in the present description means: temperature and pressure parameters within a polymerization reactor suitable for promoting polymerization between the catalyst composition and an olefin to form the desired polymer. These conditions depend on the type of polymerization used.

"production rate" or "yield" as used in the present description means: the amount of kilograms of polymer produced per gram of catalyst composition consumed in the polymerization reactor per hour, unless stated otherwise.

DETAILED DESCRIPTION OF THE PRESENT INVENTION

The novel compounds according to the present invention exhibit good results when used as internal electron donor in catalysis. In addition, the novel process for preparing these compounds according to the present invention produces these novel compounds in high yield. Furthermore, the catalyst system according to the present invention comprising said novel internal donors results in good productivity, olefins having a low XS value and a broad MWD.

As discussed above, it is desirable to obtain polypropylene having a high isotacticity. Isotacticity is determined by selection of internal and external donors. The internal donor blocks the non-stereo specific sites on the more acidic crystal planes of the catalyst. The external donor is used to counteract the acidic effect that the co-catalyst has (which is required to activate the catalyst). The external donor is preferably (somewhat) more basic than the internal donor.

Stereo regularity is (partly) determined by selection of the internal donor. Currently phthalates are used as internal donor which have health as well as environment concerns. The present invention aims at providing phthalate free donors.

It is preferred to use so-called phthalate free internal donors because of increasingly stricter government regulations about the maximum phthalate content of polymers. This leads to an increased demand in phthalate-free catalyst compositions. In the context of the present invention, "essentially phthalate-free" or "phthalate free" means having a phthalate content of less than for example 1000 ppm, more preferably less than 500 ppm, even more preferably less than 150 ppm, alternatively less than for example 100 ppm, alternatively less than for example 50 ppm, alternatively for example less than 20 ppm, such as less than 10 ppm or less than 5 ppm or even less than 1 ppm such as substantially 0 ppm, based on the total weight of the final polymer. The novel compounds according to the present invention are phthalate free.

The compounds according to the present invention may be used in a procatalyst in an amount of between 1 and 15 wt. % based on the weight of the procatalyst, preferably between 4 and 8 wt. %

In an embodiment, the process according to the present invention is carried out in a solvent, preferably an inert solvent, such as a solvent selected from the group consisting of toluene, xylene, cyclohexane and dichloromethane more preferably toluene.

The present process is as discussed above preferably carried out in the presence of a base. Examples of suitable bases are: trialkyl amines, pyridines such as pyridine or 4-dimethylaminopyridine (DMAP), metal hydrides such as sodium hydride, metal hydroxides such as sodium hydroxide and potassium hydroxide, metal carbonates such as sodium carbonate and potassium carbonate and dimethyl sulfate. Most preferably a trialkyl amine such as triethyl amine is used.

In an embodiment the present process is carried out for a duration of between 2 and 15 hours preferably between 5 and 10 hours. In an embodiment the present process is carried out at a temperature of between 0 and 140° C., preferably between 60 and 100° C., more preferably between 75 and 85° C. This temperature is the temperature of reacting the compound according to Formula II and compound according to Formula III.

Preferably in a first step the compound according to Formula III is pre-reacted with a base, preferably at room temperature, preferably by drop-wise edition of the base to a solution of a said compound according to Formula III. This pre-reaction is preferably followed by the addition of the compound according to Formula II and subsequent reaction time as stated above at the temperature stated above.

The present invention moreover relates to the use of the compound according to Formula I as an internal electron donor in a Ziegler-Natta procatalyst. The present invention moreover relates to a catalyst system for the polymerization of olefins, comprising a Ziegler-Natta procatalyst comprising Ti, Mg, a halogen, the compound according to Formula I as an internal electron donor; a co-catalyst; and optionally an external donor.

The present invention in addition relates to a process for preparing a polyolefin by contacting an olefin with the catalyst system according to the invention, the olefin being preferably propylene as well as to the polyolefin obtained by or obtainable by the process. Most preferably the present invention relates to an isotactic polypropylene. One or more of the aims discussed above are achieved by the novel compounds according to the present invention.

The present compound may be used as internal electron donors in all types of Ziegler-Natta catalysts. Some non-limiting examples thereof are specified here. Preferably, the present invention is related to a magnesium-based supported titanium halide procatalyst. The preparation therefor is discussed in more detail below.

EP 1 273 595 of *Borealis* Technology discloses a process for producing an olefin polymerisation procatalyst in the form of particles having a predetermined size range, said process comprising: preparing a solution a complex of a Gp IIa metal and an electron donor by reacting a compound of said metal with said electron donor or a precursor thereof in an organic liquid reaction medium; reacting said complex, in solution, with at least one compound of a transition metal to produce an emulsion the dispersed phase of which contains more than 50 mol % of the Gp IIa metal in said complex; maintaining the particles of said dispersed phase within the average size range 10 to 200 mu m by agitation in the presence of an emulsion stabilizer and solidifying said particles; and recovering, washing and drying said particles to obtain said procatalyst. The present compound may be used as the electron donor.

EP 0 019 330 of Dow discloses a Ziegler-Natta type catalyst composition. Said olefin polymerization catalyst composition comprising: a) a reaction product of an organo aluminium compound and an electron donor, and b) a solid component which has been obtained by halogenating a magnesium compound with the formula $MgR^1R^2$ wherein $R^1$ is an alkyl, aryl, alkoxide or aryloxide group and $R^2$ is an alkyl, aryl, alkoxide or aryloxide group or halogen, with a halide of tetravalent titanium in the presence of a halohydrocarbon, and contacting the halogenated product with a tetravalent titanium compound. The present compound may be used as the electron donor.

The Examples of U.S. Pat. No. 5,093,415 of Dow discloses an improved process to prepare a catalyst. Said process includes a reaction between titanium tetrachloride, diisobutyl phthalate, and magnesium diethoxide to obtain a solid material. This solid material is then slurried titanium tetrachloride in a solvent and phthaloyl chloride is added. The reaction mixture is heated to obtain a solid material which is reslurried in a solvent with titanium tetrachloride. Again this was heated and a solid collected. Once again the solid was reslurried once again in a solution of titanium tetrachloride to obtain a catalyst.

Example 2 of U.S. Pat. No. 6,825,146, of Dow discloses another improved process to prepare a catalyst. Said process includes a reaction between titanium tetrachloride in solution with a precursor composition—prepared by by reacting magnesium diethoxide, titanium tetraethoxide, and titanium tetrachloride, in a mixture of orthocresol, ethanol and chlorobenzene—and ethyl benzoate as electron donor. The mixture was heated and a solid was recovered. To the solid titanium tetrachloride, a solvent and benzoylchloride were added. The mixture was heated to obtain a solid product. The last step was repeated. The resulting solid procatalyst was worked up to provide a catalyst. The present compound may be used instead of or in addition to ethylbezoate.

U.S. Pat. No. 4,771,024 discloses the preparation of a catalyst on column 10, line 61 to column 11, line 9. The section "catalyst manufacture on silica" is incorporated into the present application by reference. The process comprises combining dried silica with carbonated magnesium solution (magnesium diethoxide in ethanol was bubbled with $CO_2$). The solvent was evaporated at 85° C. The resulting solid was washed and a 50:50 mixture of titanium tetrachloride and chlorobenzene was added to the solvent together with ethyl benzoate. The mixture was heated to 100° C. and liquid filtered. Again TiCl4 and chlorobenzene were added, followed by heating and filtration. A final addition of TiCl4 and chlorobenzene and benzoylchloride was carried out, followed by heating and filtration. After washing the catalyst was obtained.

WO03/068828 discloses a process for preparing a catalyst component on page 91 "preparation of solid catalyst components" which section is incorporated into the present application by reference. Magnesium chloride, toluene, epoxy chloropropane and tributyl phosphate were added under nitrogen to a reactor, followed by heating. Then phthalic anhydride was added. The solution was cooled to −25° C. and $TiCl_4$ was added dropwise, followed by heating. An internal donor was added (1,3-diphenyl-1,3-propylene glycol dibenzoate, 2-methyl-1,3-diphenyl-1,3-propylene glycol dibenzoate, 1,3-diphenyl-1,3-propylene-glycol diproprionate, or 1,3-diphenyl-2-methyl-1,3-propylene glycol diproprionate) and after stirring a solid was obtained and washed. The solid was treated with $TiCl_4$ in toluene twice, followed by washing to obtain said catalyst component. The present compound may be used as internal donor.

U.S. Pat. No. 4,866,022 discloses a catalyst component comprises a product formed by: A. forming a solution of a magnesium-containing species from a magnesium carbonate or a magnesium carboxylate; B. precipitating solid particles from such magnesium-containing solution by treatment with a transition metal halide and an organosilane having a formula: $R_nSiR'_{4-n}$, wherein n=0 to 4 and wherein R is hydrogen or an alkyl, a haloalkyl or aryl radical containing one to about ten carbon atoms or a halosilyl radical or haloalkylsilyl radical containing one to about eight carbon atoms, and R, or a halogen: C. reprecipitating such solid particles from a mixture containing a cyclic ether; and D. treating the reprecipitated particles with a transition metal compound and an electron donor. This process for preparing a catalyst is incorporated into the present application by reference. The present compound may be used as electron donor.

Preferably, the Ziegler-Natta type procatalyst in the catalyst system according to the present invention is a magnesium-based supported catalyst obtained by the process as described in WO 2007/134851 A1. In Example I the process is disclosed in more detail. Example I including all subexamples (IA-IE) is incorporated into the present description. More details about the different embodiments are disclosed starting on page 3, line 29 to page 14 line 29. These embodiments are incorporated by reference into the present description.

The process for preparing such a procatalyst comprises the following phases:

phase A): preparing a solid support for the procatalyst;

phase B): optionally activating said solid support obtained in phase A) using one or more activating compounds to obtain an activated solid support;

phase C): contacting said solid support obtained in phase A) or said activated solid support in phase B) with a catalytic species and optionally one or more internal donors and/or optionally an activator to obtain said procatalyst;

optionally Phase D: modifying said intermediate product obtained in phase C) with a Group 13- or transition metal modifier and optionally one or more internal donors.

Phase A relates to preparing a magnesium-based solid support for the catalyst. Said magnesium-containing support is known in the art as a typical component of a Ziegler-Natta procatalyst. This step of preparing a solid support for the catalyst is the same as in the prior art process. The following description explains the process of preparing magnesium-based support. Other supports may be used. Synthesis of magnesium-containing supports, such as magnesium halides, magnesium alkyls and magnesium aryls, and also magnesium alkoxy and magnesium aryloxy compounds for polyolefin production, particularly of polypropylenes production are described for instance in U.S. Pat. No. 4,978,648, WO96/32427A1, WO01/23441 A1, EP1283 222A1, EP1222 214B1; U.S. Pat. Nos. 5,077,357; 5,556,820; 4,414,132; 5,106,806 and 5,077,357 but the present process is not limited to the disclosure in these documents.

Preferably, the process for preparing the solid support for the procatalyst according to the present invention comprises the following steps: step o) preparing a Grignard reagent (optional) and step i) reacting a Grignard reagent with a silane compound.

A Grignard reagent may be prepared by contacting metallic magnesium with an organic halide as described in WO 96/32427 A1 and WO01/23441 A1. A commercial available Grignard reagent may also be used. In step i): said Grignard reagent is contacted with an alkoxy- or aryloxy-containing silane compound to give a first intermediate reaction product. Said first intermediate reaction product is a solid magnesium-containing support. Examples of these reactants are disclosed for example in WO 96/32427 A1 and WO01/23441 A1.

Preferably, said Grignard reagent is a hydrocarbyl magnesium chloride, wherein said hydrocarbyl can be an alkyl, aryl, aralkyl, alkoxide, phenoxide, etc., or mixtures thereof. Suitable examples of the hydrocarbyl group are methyl, ethyl, n-propyl, i-propyl, n-butyl, i-butyl, t-butyl, hexyl, cyclohexyl, octyl, phenyl, tolyl, xylyl, mesityl, benzyl, phenyl, naphthyl, thienyl, indolyl. In a preferred embodiment of the invention, a phenyl or butyl Grignard reagent (PhMgCl or BuMgCl) is used.

Non-limiting examples of suitable silane compounds include tetramethoxysilane, tetraethoxysilane, methyltrimethoxysilane, methyltributoxysilane, phenyltriethoxy-silane, diethyldiphenoxysilane, n-propyltriethoxysilane, diisopropyldi-methoxysilane, diisobutyldimethoxysilane, n-propyltrimethoxysilane, cyclohexyl-methyldimethoxysilane, dicyclopentyldimethoxy-silane, isobutylisopropyldimethoxyl-silane, phenyl-trimethoxysilane, diphenyl-dimethoxysilane, trifluoropropylmethyl-dimethoxysilane, bis(perhydroisoquinolino)-dimethoxysilane, dicyclohexyldimethoxy-silane, dinorbornyl-dimethoxysilane, di(n-propyl)dimethoxysilane, di(iso-propyl)-dimethoxysilane, di(n-butyl)dimethoxysilane and/or di(iso-butyl) dimethoxysilane. Preferably, tetraethoxy-silane is used as the silane compound.

Preferably, in step i) the silane-compound and the Grignard compound are introduced simultaneously to a mixing device to result in particles of the first intermediate reaction product having advantageous morphology. This is for example described in WO 01/23441 A1. Here, 'morphology' does not only refer to the shape of the particles of the solid Mg-compound and the catalyst made therefrom, but also to the particle size distribution (also characterized as span), its fines content, powder flowability, and the bulk density of the catalyst particles. Moreover, it is well known that a polyolefin powder produced in polymerization process using a catalyst system based on such procatalyst has a similar morphology as the procatalyst (the so-called "replica effect"; see for instance S. van der Ven, Polypropylene and other Polyolefins, Elsevier 1990, p. 8-10). Accordingly, almost round polymer particles are obtained with a length/diameter ratio (I/D) smaller than 2 and with good powder flowability. The Si/Mg molar ratio during step i) may range from 0.2 to 20. Preferably, the Si/Mg molar ratio is from 0.4 to 1.0.

The present inventors have found that when using the compounds according to the present invention the morphology of the support is maintained in turn leading to polymers having the same morphology. Moreover, the particle size distribution was also good.

Phase B relates to the optional step of activating said solid support and comprises step ii), being contacting the solid support with at least one activating compound selected from the group formed by activating electron donors and activating metal alkoxide compounds.

The advantage of the use of this activation step prior to contacting the solid support with the catalytic species (process phase C) is that a higher yield of polyolefins is obtained per gram of the procatalyst. Moreover, the ethylene sensitivity of the catalyst system in the copolymerisation of propylene and ethylene is also increased because of this activation step. This activation step is disclosed in detail in WO2007/134851 of the present applicant.

Examples of suitable activating electron donors are an alcohol, like ethanol or hexanol, or an ester compound, like ethyl acetate, ethyl benzoate or a phthalate ester, or an ether, like dibutylether, or pyridine. Examples of suitable metal alkoxide compounds for use in step ii) are tetraethoxy silane or tetraethoxy titanium. Preferably, a Ti-based compound, for example titanium tetraethoxide, is used together with an activating electron donor compound.

Phase C relates to the contacting of the support with a catalytic species and optionally one or more internal donors and/or one or more activators. Phase C may comprise several stages. During each of these consecutive stages the solid support is contacted with said catalytic species. In other words, the addition or reaction of said catalytic species may be repeated one or more times. When in phase D which is optional, an internal donor is added, it is not essential that a donor is also added during phase C.

For example, during stage I of phase C said solid support (first intermediate) or the activated solid support (second intermediate) is first contacted with said catalytic species and optionally subsequently with one or more internal donors. When a second stage is present, during stage II the intermediate product obtained from stage I will be contacted with additional catalytic species which may be the same or different than the catalytic species added during the first stage and optionally one or more internal donors. In case three stages are present, stage III is preferably a repetition of stage II or may comprise the contacting of the product obtained from phase II with both a catalytic species (which may be the same or different as above) and one or more internal donors. In other words, an internal donor may be added during each of these stages or during two or more of these stages. When an internal donor is added during more than one stage it may be the same or a different internal donor.

The internal electron donor is compound according to Formula I. One or more additional internal doors may be used which be any compound known in the art to be used as internal electron donor. Suitable non-limiting examples of additional internal donors are ethyl benzoate, di-n-butyl phthalate or diisobutyl phthalate, 2-ethyl-2-butyl-1,3-dimethoxypropane, 2-isopropyl-2-isopentyl-1,3-dimethoxypropane and 9,9-bis(methoxymethyl)fluorene, diethyl 2,3-di-isopropylsuccinate, diethyl 2,3-di-n-propylsuccinate, diethyl 2,3-di-isobutylsuccinate, diethyl 2,3-di-sec-butyl-succinate, dimethyl 2,3-di-isopropylsuccinate, dimethyl 2,3-di-n-propylsuccinate, dimethyl 2,3-di-isobutylsuccinate, dimethyl 2,3-di-sec-butylsuccinate, benzamides such as benzamide, methylbenzamide, and dimethylbenzamide; pentanediol dibenzoate. Since one of the aims of the present invention is to provide a phthalate free catalyst system the use of additional phthalate containing internal donor is not preferred.

An activator according to the present invention—if used—may be added either during stage I or stage II or stage III of phase C. An activator may also be added during more than one stage. Examples of suitable activators are benzamide, alkylbenzoates, and monoesters, such as benzamide, methylbenzamide, dimethylbenzamide, methyl benzoate, ethyl benzoate, ethyl acetate, and butyl acetate. Most preferably ethyl benzoate.

In a preferred embodiment of the present invention, a procatalyst is prepared having one of the donors ED I, ED II, ED III, or ED IV and ethyl benzoate as activator since the inventors have observed that this improves the activity of the catalyst and produces polymers having enhanced properties. The amount of ethyl benzoate was adjusted experimental to provide optimum activity.

Preferably, the ethoxide content in the procatalyst was low, such as at most 4 wt. %, preferably 2 wt. %, most preferably 1.5 wt. %, even more preferably at most 1 wt. % based on the total weight of the procatalyst.

Preferably, phase C comprises reacting the solid support with a transition metal halide (e.g. titanium, chromium, hafnium, zirconium, vanadium) but preferably titanium halide and optionally an internal electron donor or activator to obtain a third intermediate product.

Phase D is optional in the present invention and may comprise modifying the third intermediate product with a metal-modifier and optionally one or more internal donors to obtain a procatalyst. The modification with Group 13- or transition metal, preferably aluminium, ensures the presence of Group 13- or transition metal in the procatalyst, in addition to magnesium (from the solid support) and titanium (from the titanation treatment). After the modification step another treatment with the catalytic species is carried out, that is very similar to phase C.

The procatalyst thus prepared can be used in polymerization of olefins using an external donor and a co-catalyst. At least one compound according to Formula I is present in the procatalyst.

The catalyst system according to the present invention includes a co-catalyst. As used herein, a "co-catalyst" is a term well-known in the art in the field of Ziegler-Natta catalysts and is recognized to be a substance capable of converting the procatalyst to an active polymerization catalyst. Generally, the co-catalyst is an organometallic compound containing a metal from group 1, 2, 12 or 13 of the Periodic System of the Elements (Handbook of Chemistry and Physics, 70th Edition, CRC Press, 1989-1990). The co-catalyst may include any compounds known in the art to be used as "co-catalysts", such as hydrides, alkyls, or aryls of aluminum, lithium, zinc, tin, cadmium, beryllium, magnesium, and combinations thereof. The co-catalyst may be a hydrocarbyl aluminum co-catalyst, such as triisobutylaluminum, trihexylaluminum, di-isobutylaluminum hydride, dihexylaluminum hydride, isobutylaluminum dihydride, hexylaluminum dihydride, diisobutylhexylaluminum, isobutyl dihexylaluminum, trimethylaluminum, triethylaluminum, tripropylaluminum, triisopropylaluminum, tri-n-butylaluminum, trioctylaluminum, tridecylaluminum, tridodecylaluminum, tribenzylaluminum, triphenylaluminum, trinaphthylaluminum, and tritolylaluminum. In an embodiment, the cocatalyst is selected from triethylaluminum, triisobutylaluminum, trihexylaluminum, di-isobutylaluminum hydride and dihexylaluminum hydride. More preferably, trimethylaluminium, triethylaluminium, triisobutylaluminium, and/or trioctylaluminium. Most preferably, triethylaluminium (abbreviated as TEAL). The co-catalyst can also be a hydrocarbyl aluminum compound such as tetraethyl-dialuminoxane, methylaluminoxane, isobutylaluminoxane, tetraisobutyl-dialuminoxane, diethyl-aluminumethoxide, diisobutylaluminum chloride, methylaluminum dichloride, diethylaluminum chloride, ethylaluminum dichloride and dimethylaluminum chloride, preferably TEAL. The molar ratio of aluminum to titanium may be from about 5:1 to about 500:1 or from about 10:1 to about 200:1 or from about 15:1 to about 150:1 or from about 20:1 to about 100:1. The molar ratio of aluminum to titanium is preferably about 45:1. The aluminium/external donor molar ratio in the polymerization catalyst system preferably is from 0.1 to 200; more preferably from 1 to 100.

As external electron donors, all types of external electron donors known in the art may be used. Examples thereof are: alkylamino-alkyoxysilanes, such as diethyl-amino-triethoxysilane (DEATES); alkyl-alkoxysilanes, such as n-propyl triethoxysilane (nPTES) and n-propyl trimethoxysilane (nPTMS); imidosilanes, such as 1,1,1-triethoxy-N-(2,2,4,4-tetramethylpentan-3-ylidene) silanamine, 1,1,1-trimethoxy-N-(2,2,4,4-tetramethylpentan-3-ylidene) silanamine, and N,N,N',N'-tetramethylguanidine triethoxysilane; alkylimidosilanes, alkoxysilanes, such as dicyclopentyl dimethoxysilane, di-isopropyl dimethoxysilane, diisobutyl dimethyoxysilane, methylcyclohexyl dimethoxysilane, n-propyl trimethoxysilane, n-propyltriethoxysilane, and dimethylamino triethoxysilane.

Mixtures of external donors may be present and may include from about 0.1 mol % to about 99.9% mol % of a first external donor and from about 99.9 mol % to about 0.1 mol % of a second external donor.

In the process to prepare a polyolefin, a procatalyst, a co-catalyst, the external donor according to the present invention and the olefin can be contacted in any way known to the skilled person in the art; and as also described herein. For instance, the external donor in the catalyst system according to the present invention can be complexed with the co-catalyst and mixed with the procatalyst (pre-mix) prior to contact between the catalyst composition and the olefin. The external donor can also be added independently to the polymerization reactor. The procatalyst, the co-catalyst, and the external donor can be mixed or otherwise combined prior to addition to the polymerization reactor.

Contacting the olefin with the catalyst system according to the present invention can be done under standard polymerization conditions, known to the skilled person in the art. See for example Pasquini, N. (ed.) "Polypropylene handbook" $2^{nd}$ edition, Carl Hanser Verlag Munich, 2005. Chapter 6.2 and references cited therein. The polymerization process may be a gas phase, a slurry or a bulk polymerization process, operating in one or more than one reactor. One or more olefin monomers can be introduced in a polymerization reactor to react with the catalyst composition and to form an olefin-based polymer (or a fluidized or agitated bed of polymer particles).

In the case of polymerization in a slurry (liquid phase), a dispersing agent is present. Suitable dispersing agents include for example propane, n-butane, isobutane, n-pentane, isopentane, hexane (e.g. iso- or n-), heptane (e.g. isoor n-), octane, cyclohexane, benzene, toluene, xylene, liquid propylene and/or mixtures thereof. The polymerization such as for example the polymerization temperature and time, monomer pressure, avoidance of contamination of catalyst, choice of polymerization medium in slurry processes, the use of further ingredients (like hydrogen) to control polymer molar mass, and other conditions are well known to persons of skill in the art. The polymerization temperature may vary within wide limits and is, for example for propylene polymerization, from 0° C. to 120° C., preferably from 40° C. to 100° C. The pressure during (propylene) (co)polymerization is for instance from 0.1 to 6 MPa, preferably from 1 to 4 MPa.

Several types of polyolefins may prepared such as homopolyolefins, random copolymers and heterophasic polyolefin. The for latter, and especially heterophasic polypropylene, the following is observed.

Heterophasic propylene copolymers are generally prepared in one or more reactors, by polymerization of propylene and optionally one or more other olefins, for example ethylene, in the presence of a catalyst and subsequent polymerization of a propylene-α-olefin mixture. The resulting polymeric materials can show multiple phases (depending on monomer ratio), but the specific morphology usually depends on the preparation method and monomer ratio. The heterophasic propylene copolymers employed in the process according to present invention can be produced using any conventional technique known to the skilled person, for example multistage process polymerization, such as bulk polymerization, gas phase polymerization, slurry polymerization, solution polymerization or any combinations thereof. Any conventional catalyst systems, for example, Ziegler-Natta or metallocene may be used. Such techniques and catalysts are described, for example, in WO06/010414; Polypropylene and other Polyolefins, by Ser van der Ven, Studies in Polymer Science 7, Elsevier 1990; WO06/010414, U.S. Pat. Nos. 4,399,054 and 4,472,524.

The molar mass of the polyolefin obtained during the polymerization can be controlled by adding hydrogen or any other agent known to be suitable for the purpose during the polymerization. The polymerization can be carried out in a continuous mode or batch-wise. Slurry-, bulk-, and gas-phase polymerization processes, multistage processes of each of these types of polymerization processes, or combinations of the different types of polymerization processes in a multistage process are contemplated herein. Preferably, the polymerization process is a single stage gas phase process or a multistage, for instance a two-stage gas phase process, e.g. wherein in each stage a gas-phase process is used or including a separate (small) prepolymerization reactor.

Examples of gas-phase polymerization processes include both stirred bed reactors and fluidized bed reactor systems; such processes are well known in the art. Typical gas phase olefin polymerization reactor systems typically comprise a reactor vessel to which an olefin monomer(s) and a catalyst system can be added and which contain an agitated bed of growing polymer particles. Preferably the polymerization process is a single stage gas phase process or a multistage, for instance a 2-stage, gas phase process wherein in each stage a gas-phase process is used. As used herein, "gas phase polymerization" is the way of an ascending fluidizing medium, the fluidizing medium containing one or more monomers, in the presence of a catalyst through a fluidized bed of polymer particles maintained in a fluidized state by the fluidizing medium optionally assisted by mechanical agitation. Examples of gas phase polymerization are fluid bed, horizontal stirred bed and vertical stirred bed. "fluidbed," "fluidized," or "fluidizing" is a gas-solid contacting process in which a bed of finely divided polymer particles is elevated and agitated by a rising stream of gas optionally assisted by mechanical stirring. In a "stirred bed" upwards gas velocity is lower than the fluidization threshold. A typical gas-phase polymerization reactor (or gas phase reactor) include a vessel (i.e., the reactor), the fluidized bed, a product discharge system and may include a mechanical stirrer, a distribution plate, inlet and outlet piping, a compressor, a cycle gas cooler or heat exchanger. The vessel may include a reaction zone and may include a velocity reduction zone, which is located above the reaction zone (viz. bed). The fluidizing medium may include propylene gas and at least one other gas such as an olefin and/or a carrier gas such as hydrogen or nitrogen. The contacting can occur by way of feeding the catalyst composition into the polymerization reactor and introducing the olefin into the polymerization reactor. In an embodiment, the process includes contacting the olefin with a co-catalyst. The co-catalyst can be mixed with the procatalyst (pre-mix) prior to the introduction of the procatalyst into the polymerization reactor. The co-catalyst may be also added to the polymerization reactor independently of the procatalyst. The independent introduction of the co-catalyst into the polymerization reactor can occur (substantially) simultaneously with the procatalyst feed. An external donor may also be present during the polymerization process.

The olefin according to the invention may be selected from mono- and di-olefins containing from 2 to 40 carbon atoms. Suitable olefin monomers include alpha-olefins, such as ethylene, propylene, alpha-olefins having from 4 to 20 carbonatoms (viz. C4-20), such as 1-butene, 1-pentene, 1-hexene, 4-methyl-1-pentene, 1-heptene, 1-octene, 1-decene, 1-dodecene and the like; C4-C20 diolefins, such as 1,3-butadiene, 1,3-pentadiene, norbornadiene, 5-vinyl-2-norbornene (VNB), 1,4-hexadiene, 5-ethylidene-2-norbornene (ENB) and dicyclopentadiene; vinyl aromatic compounds having from 8 to 40 carbon atoms (viz. C8-C40) including styrene, o-, m- and p-methylstyrene, divinylbenzene, vinylbiphenyl, vinylnapthalene; and halogen-substituted C8-C40 vinyl aromatic compounds such as chlorostyrene and fluorostyrene.

Preferably, the olefin is propylene or a mixture of propylene and ethylene, to result in a propylene-based polymer, such as propylene homopolymer or propylene-olefin copolymer, most preferably isotactic homopolypropylene. The olefin may an alpha-olefin having up to 10 carbon atoms, such as ethylene, butene, hexene, heptene, octene. A propylene copolymer is herein meant to include both so-called random copolymers which typically have relatively low comonomer content, e.g. up to 10 mol %, as well as so-called impact PP copolymers or heterophasic PP copolymers comprising higher comonomer contents, e.g. from 5 to 80 mol %, more typically from 10 to 60 mol %. The impact PP copolymers are actually blends of different propylene polymers; such copolymers can be made in one or two reactors and can be blends of a first component of low comonomer content and high crystallinity, and a second component of high comonomer content having low crystallinity or even rubbery properties. Such random and impact copolymers are well-known to the skilled in the art. A propylene-ethylene random copolymer may be produced in one reactor. Impact PP copolymers may be produced in two reactors: polypropylene homopolymer may be produced in a first reactor; the content of the first reactor is subsequently transferred to a second reactor into which ethylene (and optionally propylene) is introduced. This results in production of a propylene-ethylene copolymer (i.e. an impact copolymer) in the second reactor.

The present invention also relates to a polyolefin, preferably a polypropylene obtained or obtainable by a process, comprising contacting an olefin, preferably propylene or a mixture of propylene and ethylene with the procatalyst according to the present invention.

In one embodiment the present invention relates to the production of a homopolymer of polypropylene. The donors according to the present invention allow for the preparation of a polypropylene having high isotacticity and low XS values and improved bulk density without significant generation of fines.

The polyolefin, preferably the polypropylene according to the present invention has a molecular weight distribution higher than 3.5, preferably higher than 4, more preferably higher than 4.5 and for instance below 10 or below 9 or even below 6. The molecular weight distribution of the polyolefins, preferably polypropylene according to the present invention is for instance from 3.5 to 9, preferably from 4 to 8, or from 4 to 6, more preferably from 4.5 to 6. Xylene soluble fraction (XS) is preferably from about 0.5 wt % to about 10 wt %, or from about 1 wt % to about 8 wt %, or from 2 to 6 wt %, or from about 1 wt % to about 5 wt %. Preferably, the xylene amount (XS) is lower than 6 wt %, preferably lower than 5 wt %, more preferably lower than 4 wt % or even lower than 3 wt % and most preferably lower than 2.7 wt %. The bulk density is preferably at least 360 g/100 ml, more preferably at least 380, even more preferably at least 400 g/100 ml. The production rate is preferably from about 1 kg/g/hr to about 100 kg/g/hr, or from about 10 kg/g/hr to about 40 kg/g/hr. The isotacticity of the polymer may be expressed as a maximum amount of atactic polymer in the total amount of polymer produced, preferably in an amount of less than 3 wt. %, preferably less than 2 wt. % or even 1 wt. %, based on the total amount of polymer. The isotacticity may also be expressed as a minimal amount of isotactic polymer in the total amount of polymer produced, preferably at least 97 wt. %, preferably at least 98 wt. % or even at least 99 wt. %, based on the total amount of polymer.

The olefin polymer obtained in the present invention is considered to be a thermoplastic polymer. The thermoplastic polymer composition according to the invention may also contain one or more of usual additives, like those mentioned above, including stabilisers, e.g. heat stabilisers, anti-oxidants, UV stabilizers; colorants, like pigments and dyes; clarifiers; surface tension modifiers; lubricants; flame-retardants; mould-release agents; flow improving agents; plasticizers; anti-static agents; impact modifiers; blowing agents; fillers and reinforcing agents; and/or components that enhance interfacial bonding between polymer and filler, such as a maleated polypropylene, in case the thermoplastic polymer is a polypropylene composition. The skilled person can readily select any suitable combination of additives and additive amounts without undue experimentation. The amount of additives depends on their type and function; typically is of from 0 to about 30 wt %; preferably of from 0 to about 20 wt %; more preferably of from 0 to about 10 wt % and most preferably of from 0 to about 5 wt % based on the total composition. The sum of all components added in a process to form the polyolefins, preferably the propylene-base polymers or compositions thereof should add up to 100 wt %.

The thermoplastic polymer composition of the invention may be obtained by mixing one or more of the thermoplastic polymers with one or more additives by using any suitable means. Preferably, the thermoplastic polymer composition of the invention is made in a form that allows easy processing into a shaped article in a subsequent step, like in pellet or granular form. The composition can be a mixture of different particles or pellets; like a blend of a thermoplastic polymer and a master batch of nucleating agent composition, or a blend of pellets of a thermoplastic polymer comprising one of the two nucleating agents and a particulate comprising the other nucleating agent, possibly pellets of a thermoplastic polymer comprising said other nucleating agent. Preferably, the thermoplastic polymer composition of the invention is in pellet or granular form as obtained by mixing all components in an apparatus like an extruder; the advantage being a composition with homogeneous and well-defined concentrations of the nucleating agents (and other components).

The invention also relates to the use of the polyolefins, preferably the propylene-based polymers (also called polypropylenes) according to the invention in injection moulding, blow moulding, extrusion moulding, compression moulding, casting, thin-walled injection moulding, etc. for example in food contact applications or automotive application. Furthermore, the invention relates to a shaped article comprising the polyolefin, preferably the propylene-based polymer according to the present invention.

The polyolefin, preferably the propylene-based polymer according to the present invention may be transformed into shaped (semi)-finished articles using a variety of processing techniques. Examples of suitable processing techniques include injection moulding, injection compression moulding, thin wall injection moulding, extrusion, and extrusion compression moulding. Injection moulding is widely used to produce articles such as for example caps and closures, batteries, pails, containers, automotive exterior parts like bumpers, automotive interior parts like instrument panels, or automotive parts under the bonnet. Extrusion is for example widely used to produce articles, such as rods, sheets, films and pipes. Thin wall injection moulding may for example be used to make thin wall packaging applications both for food and non-food segments.

Additional Aspects and Embodiments

The present invention moreover relates to the clauses stated below.
1. A compound according to Formula I wherein $R^1$ is a hydrocarbyl group selected from the group consisting of alkyl, alkenyl, aryl, aralkyl, and alkylaryl groups, and one or more combinations thereof; wherein $R^2$ is a hydrogen atom, an aryl group or an alkyl group; and wherein $R^3$, $R^4$, $R^5$ and $R^6$, are the same or different and are each independently a hydrogen atom, a halogen atom, a cyano group, an amino group a hydrocarbyl group selected from the group consisting of alkyl, alkenyl, aryl, aralkyl, and alkylaryl groups or an alkoxy group, and one or more combinations thereof.
2. The compound according to clause 1, wherein $R^1$=phenyl, $R^2$=methyl; $R^3$=hydrogen; $R^4$=hydrogen; $R^5$=hydrogen; and $R^6$=hydrogen, the compound being 2-(N-methylbenzamido) phenyl benzoate.
3. Use of the compound according to any one of clauses 1-2 as an internal electron donor in a Ziegler-Natta type catalyst system.
4. Ziegler-Natta type procatalyst comprising Ti, Mg, a halogen, an internal electron donor being the compound according to any one of clauses 1-2.
5. A catalyst system for the polymerization of olefins, comprising a Ziegler-Natta type procatalyst according to clause 4; a co-catalyst; and an external donor.
6. A process for preparing a polyolefin by contacting an olefin with the catalyst system according to clause 4, the olefin being preferably propylene.
7. A polyolefin obtained by or obtainable by the process according to clause 6.

It is noted that the invention relates to all possible combinations of features recited in the claims. Features described in the description may further be combined. Although the invention has been described in detail for purposes of illustration, it is understood that such detail is solely for that purpose and variations can be made therein by those skilled in the art without departing from the spirit and scope of the invention as defined in the claims. It is further noted that the term 'comprising' does not exclude the presence of other elements. However, it is also to be understood that a description on a product comprising certain components also discloses a product consisting of these components. Similarly, it is also to be understood that a description on a process comprising certain steps also discloses a process consisting of these steps. The invention will be further elucidated with the following examples without being limited hereto.

EXAMPLES

Preparation of EDI: Synthesis of 2-(N-methylbenzamido) phenyl benzoate

EDI was prepared according to the reaction scheme shown below starting from 2-methyl-aminophenol and benzoyl chloride:

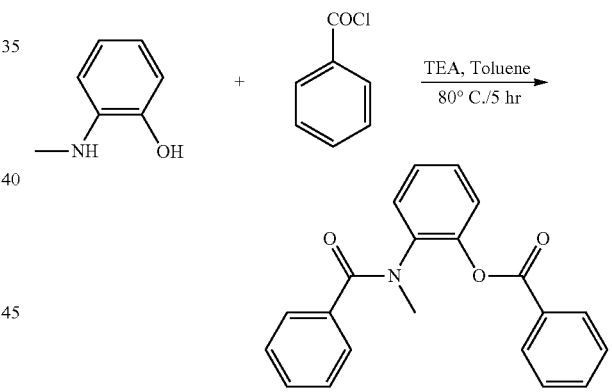

A three neck round bottom flask fitted with a condenser, an addition funnel and a magnetic stirrer was charged with 2-methyl-aminophenol (5.0 grams, 0.04 moles) in toluene (75 ml, 20 equiv.). This solution was stirred and then triethylamine (9 grams, 0.089 moles) was added drop wise. After the addition of triethylamine was completed, the reaction mixture was stirred for a period of between 15 to 20 minutes at room temperature. To the resulting reaction mixture benzoyl chloride (12.5 grams, 0.089 moles) in toluene (20 ml) was added drop wise through the addition funnel over a period of ½ hour. After complete addition of the benzoyl chloride, the reaction mixture was heated to a temperature of 80° C. for a period of 5 hours. The completion of the reaction was monitored using TLC. The reaction mixture was filtered on a silica (Celite®) bed to remove any formed triethyl amine hydrochloride. The filtrate was collected, washed with water (3 times 100 ml), a brine solution and then dried over dry sodium sulfate. The resulting filtrate was evaporated using a rotary evaporator under reduced pressure. The residue obtained was crystallized from hexane to obtain brown crystals of EDI. The purity of the compound determined by HPLC was >98.8%. The mass of the compound was observed using LCMS 332.6 (M+1) compare to the theoretical mass 331.3.

Preparation of ED II: Synthesis of 2-benzamido-4-(tert-butyl) phenyl benzoate

ED II was prepared according to the reaction scheme shown below starting from 2-amino-4-(tert-butyl) phenol and benzoyl chloride:

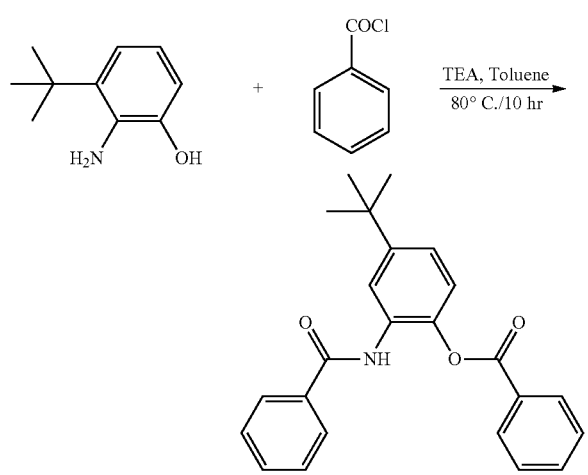

A three neck round bottom flask fitted with a condenser, an addition funnel and a magnetic stirrer was charged with 2-amino-4-(tert-butyl) phenol (20 grams, 0.1210 moles) in toluene (220 ml, 20 equiv.). This solution was stirred and then triethylamine (24.5 grams, 0.2421 moles) was added drop wise. After the addition of triethylamine was completed, the reaction mixture was stirred for a period of between 15 to 20 minutes at room temperature. To the resulting reaction mixture benzoyl chloride (34.03 grams, 0.2421 moles) in toluene (50 ml) was added drop wise through the addition funnel over a period of 1 hour. After complete addition of the benzoyl chloride, the reaction mixture was heated to a temperature of 80° C. for a period of 10 hours. The completion of the reaction was monitored using TLC. The hot reaction mixture was filtered on a silica (Celite®) bed to remove any formed triethyl amine hydrochloride. The filtrate was cooled and the solid separated was filtered. The solid material was washed with cold toluene and with hexane. The solid material was dried to obtain ED II as a white solid. The purity of the compound determined by HPLC was >99%. The IR spectrum showed three characteristic peaks for amide (—NH stretching), ester carbonyl and amide carbonyl at 3263 cm$^{-1}$, 1729 cm$^{-1}$ and 1648 cm$^{-1}$ respectively. The mass of the compound was observed using GCMS was 373.03 compared to the theoretical mass 373.45.

Preparation of ED III: Synthesis of 4-(tert-butyl)-2-(N-methylbenzamido) phenyl benzoate ED III was prepared in two steps according to the reaction schemes shown below starting from 2-amino-4-(tert-butyl) phenol and benzoyl chloride:

Step 1: Preparation of 4-(tert butyl)-2-aminophenol

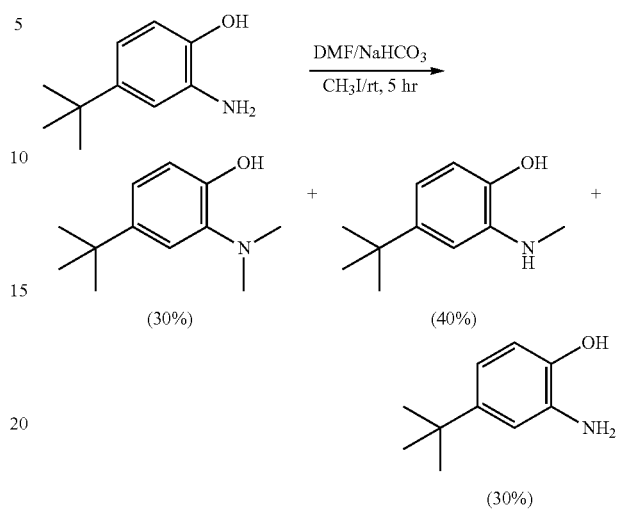

A solution of 4-(tert butyl)-2-aminophenol (20 grams, 0.121 moles) in dry DMF (75 ml) was treated with NaHCO$_3$ (10.68 gram, 0.127 moles) and CH$_3$I (20.95 gram, 0.148 moles) and stirred at room temperature for 5 hours. After workup the residue was purified using silica gel flash chromatography (using as eluent a mixture of petroleum ether/ethyl acetate, 5:1) to afford 4-(tert butyl)-2-aminophenol as a white solid (40%).

Step 2: Preparation of 4-(tert-butyl)-2-(N-methylbenzamido) phenyl benzoate

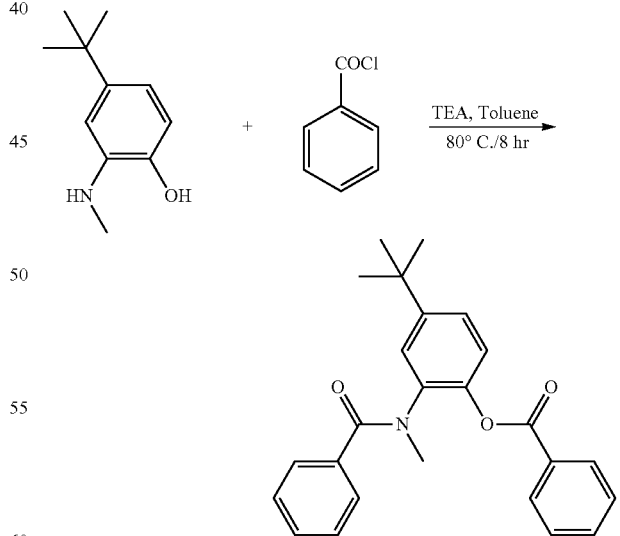

A three neck round bottom flask fitted with a condenser, an addition funnel and a magnetic stirrer was charged with 4-(tert-butyl)-2-(methylamino) phenol (20 grams, 0.1210 moles) in toluene (220 ml, 20 equiv.). This solution was stirred and then triethylamine (3.10 grams, 0.0307 moles) was added drop wise. After the addition of triethylamine was completed, the reaction mixture was stirred for a period of between 15 to 20 minutes at room temperature. To the resulting reaction mixture benzoyl chloride (4.31 grams, 0.0307 moles) in toluene (10 ml) was added drop wise through the addition funnel over a period of 10 minutes. After complete addition of the benzoyl chloride, the reaction mixture was heated to a temperature of 80° C. for a period of 8 hours. The completion of the reaction was monitored using TLC. The hot reaction mixture was filtered on a silica (Celite®) bed to remove any formed triethyl amine hydrochloride. The filtrate was cooled and the solid separated was filtered. The solid material was washed with hexane. The solid material was dried to obtain ED III as a solid. The purity of the compound determined by HPLC was >98.8%. The mass of the compound was observed using LCMS was 388.6 compared to the theoretical mass 387.48.

Preparation of ED IV: Synthesis of 4-(tert-butyl)-2-(N-methylbenzamido)-6-methyl phenyl benzoate EDIV was prepared in two steps according to the reaction schemes shown below starting from 2-amino-4-(tert-butyl)-6-methyl phenol and benzoyl chloride:

Step 1: Preparation of 4-(tert butyl)-2-aminophenol

Step 2: Preparation of 4-(tert-butyl)-6-methyl-2-(N-methylbenzamido) phenyl benzoate

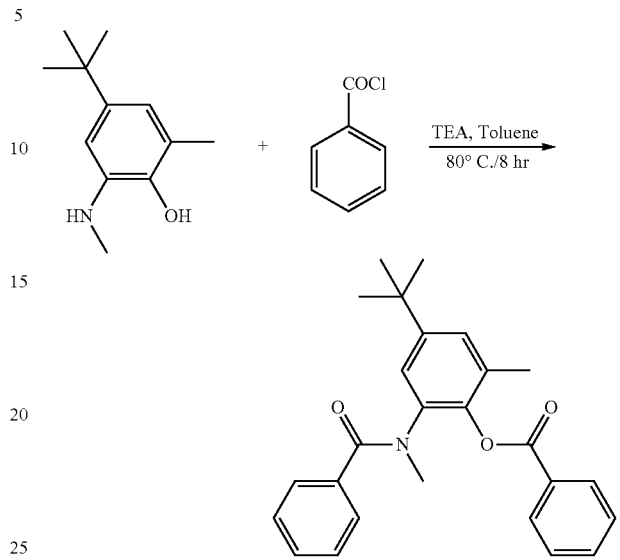

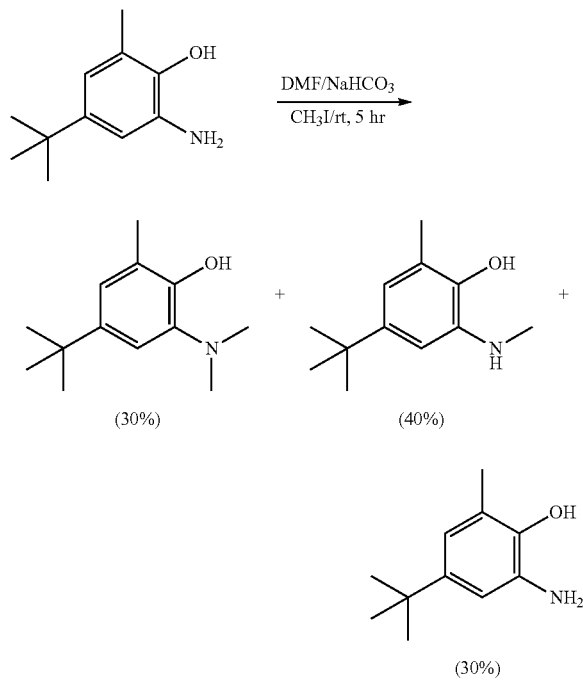

A three neck round bottom flask fitted with a condenser, an addition funnel and a magnetic stirrer was charged with 4-(tert-butyl)-6-methyl-2-(methylamino) phenol (5 grams, 0.0279 moles) in toluene (80 ml, 20 equiv.). This solution was stirred and then triethylamine (6.21 grams, 0.0614 moles) was added drop wise. After the addition of triethylamine was completed, the reaction mixture was stirred for a period of between 15 to 20 minutes at room temperature. To the resulting reaction mixture benzoyl chloride (8.63 grams, 0.0614 moles) in toluene (10 ml) was added drop wise through the addition funnel over a period of 10 minutes. After complete addition of the benzoyl chloride, the reaction mixture was heated to a temperature of 80° C. for a period of 8 hours. The completion of the reaction was monitored using TLC. The hot reaction mixture was filtered on a silica (Celite®) bed to remove any formed triethyl amine hydrochloride. The filtrate was cooled and the solid separated was filtered. The solid material was washed with hexane. The solid material was dried to obtain ED III as a solid.

The materials used were received from Sigma-Aldrich. All materials and reagents used for analysis were of high purity. The reactions were monitored by thin layer chromatography (TLC). The purity of the compounds was analyzed by HPLC. Compounds were characterized by a liquid chromatograph-mass spectrometer (LC-MS) system, comprising a liquid chromatograph and a Quattro Ultima Pt mass spectrometer. An Xterra C18 (50 mm×4.6 mm; 5 microns) column was used for separating the components by liquid chromatography.

Preparation of Ziegler-Natta Catalyst

An activated magnesium chloride support was prepared according to the procedure described in Example I of WO 2007/134851A1. Subsequently, this activated support was subjected to three treatments with titanium tetrachloride according to the procedure described in WO 2007/134851A1 and an internal donor according to the invention.

A solution of 4-(tert butyl)-6-methyl-2-aminophenol (20 grams, 0.121 moles) in dry DMF (75 ml) was treated with NaHCO₃ (10.68 gram, 0.127 moles) and CH₃I (20.95 gram, 0.148 moles) and stirred at room temperature for 5 hours. After workup the residue was purified using silica gel flash chromatography (using as eluent a mixture of petroleum ether/ethyl acetate, 5:1) to afford 4-(tert butyl)-6-methyl-2-aminophenol as a white solid (40%).

Four different types of catalysts were prepared each having a different internal donor.

The activity was tested of a comparative donor, dibutyl phthalate and of three of the donors according to the present invention, viz. 2-(N-methylbenzamido) phenyl benzoate (EDI), 2-benzamido-4-(tert-butyl) phenyl benzoate (EDII) and 4-(tert-butyl)-2-(N-methylbenzamido) phenyl benzoate (EDIII).

Polymerization Reactions

Polymerization is carried out using a two-liter autoclave vessel, which is baked at 130° C., for 60 minutes under a continuous purge of nitrogen prior to any polymerization reaction. Liquid propylene (1375 gram) was pumped in to the autoclave reactor at room temperature. The reactor was pressurized to 200 psi with hydrogen and raised the temperature to 62° C. To this preheated autoclave, an external donor (cyclohexylmethyl dimethoxysilane or C-donor), tri-ethyl aluminium (co-catalyst), followed by the synthesized Zeigler-Natta catalyst, which was slurred in isooctane solvent. The reactor temperature was raised to 67° C., pressure should maintain to 400 psi and the speed of rotation should be 500-600 rpm. Propylene polymerization was carried out for 60 minutes; with propylene supplied continuously to maintain the total reactor pressure at 400 psi.

TABLE 1

| Internal donor | Productivity kg/gcat · hour | XS (%) | MWD |
|---|---|---|---|
| Dibutyl phthalate (C) | 27.1 | 2-3 | |
| ED I | 8.4 | 20 | 5.6 |
| ED II | 8-10 | 4-6.5 | |
| ED III | 22.5 | 2.44 | |

For ED I it is clear that compared to the phthalate containing donor (C) the productivity is decreased to 8.4 Kg/g·cat·hour and the xylene solubility is increased to 20%. A broad molecular weight distribution of 5.6 is obtained.

Interestingly, it was observed that the ethoxide content of the catalyst during the catalyst preparation was high (2.20%), which indicates that ED I showed trans-esterification during the catalyst preparation step.

When there is a substituent on the aromatic system like tertiary butyl group namely 2-benzamido-4-(tert-butyl) phenyl benzoate (ED III compared to ED I) it is clear that the productivity rises and the XS decreases. When a tertiary butyl group is present with (ED III) and without (ED II) a methyl substituent on the nitrogen atom, the following is observed. When there is a free hydrogen on the nitrogen atom there is decrease in the productivity and a slight decrease in xylene solubility. However, when comparing ED I with ED II it is clear that even with a free hydrogen atom on the nitrogen atom better results are obtained, especially for XS due to the aromatic substituent.

During catalyst preparation using the compound (ED II) showed less ethoxide content. The presence of less ethoxide in the catalyst reflects in terms of improvement in the productivity and good xylene solubility. Further substitution of the alkyl group like methyl on compound (ED II) namely, 4-(tert-butyl)-2-(N-methylbenzamido) phenyl benzoate (ED III), showed very good productivity 22.5 kgPP/g·cat and excellent xylene solubility 2.44%. The ethoxide content of the catalyst, prepared using compound (ED III) is very low 1.21%. From these observation it is clear that the alkyl substituent on the parent aromatic system is preferred and also it very much preferred to have an alkyl substituent on the nitrogen. The free hydrogen on the nitrogen may interfere during the polymerization step leading to less than optimal results.

Additional catalysts were prepared using the novel compounds according to the present invention as internal electron donor as discussed below. A procatalyst was prepared according to the process in WO 2007/134851A1. Instead of aminobenzoate (AB) as the internal donor as discussed in WO 2007/134851A1, either donor ED I, ED II or ED III were used. As a support (S) either magnesium based support based on a phenyl Grignard (support I) or based on a butyl Grignard (support II) is used. In the table below it is clear which support is used. In three examples no activator was used during phase C of the process. It is however produced due to trans-esterification and that is why the Table below shows presence of activator in the final catalyst. During three of the examples ethyl benzoate (EB) was used as an activator (ACT). Polymerizations were carried out using 20 mg of catalyst, 2 ml of triethyl aluminium as procatalyst, 1.375 kg of propylene, a temperature of 67° C. and a total pressure of 24 bar, the hydrogen pressure of 200 psi, a duration of 1 hour and the addition of 50 µl cyclohexylmethyl dimethoxysilane (C-donor) as the external donor. The amount of xylene soluble has been determined as well as the activity of which are both in the table. Moreover the bulk density (BD in g/100 ml), isotacticity (Isotact. in %) and percentage of fines determined through sieving analyses was also determined.

| S | ACT | ID | % ID | % Ti | % Mg | % ACT | Activity | XS | BD | Isotact.. | Fines |
|---|---|---|---|---|---|---|---|---|---|---|---|
| I | No | EDI | 0.1 | 3.55 | 20.75 | 2.2 | 8.4 | 20.0 | — | — | — |
| I | No | EDII | 3.4 | 2.68 | 19.41 | 1.2 | 8.1 | 8.6 | ND | — | — |
| I | No | EDIII | 4.6 | 2.45 | 18.59 | 0.6 | 16.8 | 2.43 | 390 | — | 1.4 |
| I | EB | EDII | 4.2 | 3.59 | 18.43 | 6.23 | 10.2 | 3.1 | 336 | 94.8 | 1.2 |
| I | EB | EDIII | 6.1 | 2.63 | 18.41 | 5.4 | 22.5 | 2.44 | 411 | 97.8 | <1 |
| II | EB | EDIII | 5.7 | 2.37 | 19.3 | 4.7 | 21.2 | 4.2 | 408 | 96.2 | <1 |

From these data it is clear that when comparing support I using ED II with and without activator an increase in activity (in Kg PP/g cat), a decrease in xylene soluble (in wt. %) is observed which leads to the conclusion that a combination of a ethyl benzoate as an activator and a compound according to Formula I according to the present invention provides improved results compared to a procatalyst without the use of an activator. Thus a procatalyst is preferred wherein an activator, preferably a monoester activator, more preferably ethyl benzoate is present. When the results for ED I, ED II and ED III are compared it is clear that going from ED II to ED I to ED III the activity increases and going from ED I to ED II to ED III the xylene solubles decrease. These data are all for the catalysts without activator. When ED II and ED III are compared using ethyl benzoate as activator it is clear that the activity increases, the XS decreases and the bulk density increases as well as the isotacticity. This clearly shows that ED III shows better results than ED II which is related to the presence of the methyl group on the amine. In order to test the effect of the use of the Grignard reagent using a support manufacture the last two entries of the table above can be compared which show that the activity slightly decreases and the XS increases going from the phenyl based support to a butyl based support. Both cases show however a low amount of fines. It is hence shown that both a phenyl based support and a butyl based support may be used in a catalyst together with the novel compounds according to the present invention as internal electron donors to prepare polyolefins, such as PP. From the above it is clear that the new compounds according to the present invention are suitable for use as internal electron donors. The present invention is further defined by the appended claims.

The invention claimed is:

1. A process for the synthesis of a compound according to Formula I

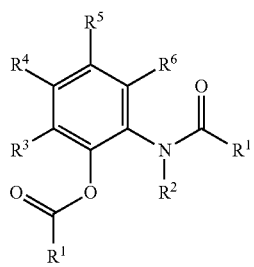

Formula I wherein $R^1$ is a hydrocarbyl group selected from alkyl, alkenyl, aryl, aralkyl, alkylaryl groups, or one or more combinations thereof; wherein $R^2$ is a hydrogen atom, an aryl group or an alkyl group; and wherein $R^3$, $R^4$, $R^5$ and $R^6$ are the same or different and are each independently a hydrogen atom, a halogen atom, a cyano group, an amino group, a hydrocarbyl group selected from alkyl, alkenyl, aryl, aralkyl, or alkylaryl groups, or an alkoxy group, or one or more combinations thereof; said process comprising the step of reacting a compound according to Formula II:

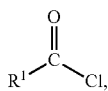

wherein $R^1$ is as above, with a compound according to Formula III:

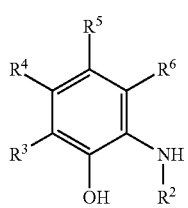

Formula III wherein $R^2$-$R^6$ are as above, to obtain the compound according to Formula I.

2. The process according to claim 1, wherein $R^2$ is hydrogen or methyl.
3. The process according to claim 1, wherein $R^2$ is methyl.
4. The process according to claim 1, wherein $R^1$ is phenyl.
5. The process according to claim 1 wherein at least two of $R^3$, $R^4$, $R^5$ and $R^6$ are hydrogen.
6. The process according to claim 1 wherein $R^3$, $R^4$, and $R^6$ are hydrogen.
7. The process according to claim 1 wherein at least one of $R^3$, $R^4$, $R^5$ and $R^6$ is an alkyl.
8. The process according to claim 1 wherein at least one of $R^3$, $R^4$, $R^5$ and $R^6$ is tert-butyl.
9. The process according to claim 1, wherein $R^5$ is tert-butyl.
10. A compound according to Formula I:

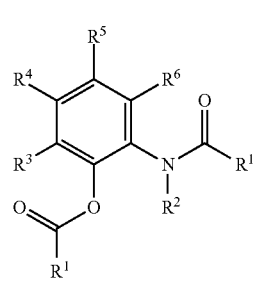

Formula I wherein $R^1$ is phenyl, $R^2$ is hydrogen; $R^3$ is hydrogen; $R^4$ is hydrogen; $R^5$ is tert-butyl; and $R^6$ is hydrogen, the compound being 2-benzamide-4-(tert-butyl) phenyl benzoate.

11. A compound according to Formula I:

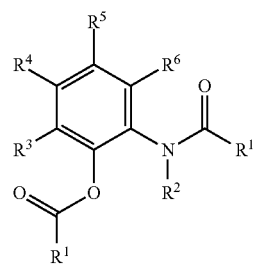

Formula I wherein $R^1$ is phenyl, $R^2$ is methyl; $R^3$ is hydrogen; $R^4$ is hydrogen; $R^5$ is tert-butyl; and $R^6$ is hydrogen, the compound being 4-(tert-butyl)-2-(N-methylbenzamido) phenyl benzoate.

12. A compound according to Formula I:

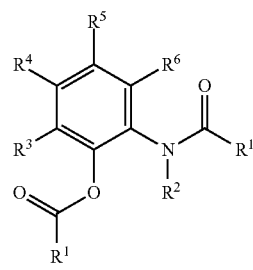

Formula I wherein $R^1$ is phenyl, $R^2$ is methyl; $R^3$ is methyl; $R^4$ is hydrogen; $R^5$ is tert-butyl; and $R^6$ is hydrogen, the compound being 4-(tert-butyl)-2-(N-methylbenzamido)-6-methyl phenyl benzoate.

13. A Ziegler-Natta procatalyst comprising Ti, Mg, a halogen, an internal electron donor being a compound prepared according to the process of claim 1 or a compound according to Formula I

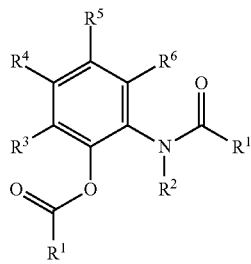

Formula I wherein $R^1$ is a hydrocarbyl group selected from alkyl, alkenyl, aryl, aralkyl, or alkylaryl groups, or one or more combinations thereof; wherein $R^2$ is a hydrogen atom, an aryl group or an alkyl group; and wherein $R^3$, $R^4$, $R^5$ and $R^6$, are the same or different and are each independently a hydrogen atom, a halogen atom, a cyano group, an amino group, a hydrocarbyl group selected from alkyl, alkenyl, aryl, aralkyl, or alkylaryl groups, or an alkoxy group, or one or more combinations thereof.

14. A catalyst system for the polymerization of olefins, comprising a Ziegler-Natta procatalyst according to claim 13; a co-catalyst; and an external donor.

15. A process for preparing a polyolefin comprising contacting an olefin with the catalyst system according to claim 14.

16. The process according to claim 15, wherein the olefin is propylene.

17. A polyolefin obtained by the process according to claim 15.

18. A Ziegler-Natta procatalyst comprising Ti, Mg, a halogen, an internal electron donor being a compound according to Formula I

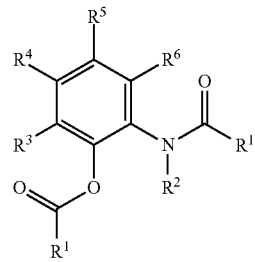

Formula I wherein $R^1$ is phenyl, $R^2$ is methyl; $R^3$ is hydrogen; $R^4$ is hydrogen; $R^5$ is hydrogen; and $R^6$ is hydrogen, the compound being 2-(N-methylbenzamido) phenyl benzoate; or wherein $R^1$ is phenyl, $R^2$ is hydrogen; $R^3$ is hydrogen; $R^4$ is hydrogen; $R^5$ is tert-butyl; and $R^6$ is hydrogen, the compound being 2-benzamide-4-(tert-butyl) phenyl benzoate; or wherein $R^1$ is phenyl, $R^2$ is methyl; $R^3$ is hydrogen; $R^4$ is hydrogen; $R^5$ is tert-butyl; and $R^6$ is hydrogen, the compound being 4-(tert-butyl)-2-(N-methylbenzamido) phenyl benzoate; or wherein $R^1$ is phenyl, $R^2$ is methyl; $R^3$ is methyl; $R^4$ is hydrogen; $R^5$ is tert-butyl; and $R^6$ is hydrogen, the compound being 4-(tert-butyl)-2-(N-methylbenzamido)-6-methyl phenyl benzoate.

* * * * *